(12) United States Patent
Arlen et al.

(10) Patent No.: US 7,491,801 B2
(45) Date of Patent: Feb. 17, 2009

(54) IDENTIFICATION AND DEVELOPMENT OF SPECIFIC MONOCLONAL ANTIBODIES TO SQUAMOUS CELL CARCINOMA

(75) Inventors: Myron Arlen, Great Neck, NY (US); Kwong Y. Tsang, Bethesda, MD (US)

(73) Assignee: International Bioimmune Systems, Inc., Great Neck, NY (US)

( * ) Notice: Subject to any disclaimer, the term of this patent is extended or adjusted under 35 U.S.C. 154(b) by 524 days.

(21) Appl. No.: 10/363,095

(22) PCT Filed: Aug. 28, 2001
(Under 37 CFR 1.47)

(86) PCT No.: PCT/US01/26734

§ 371 (c)(1),
(2), (4) Date: Dec. 29, 2003

(87) PCT Pub. No.: WO02/20617

PCT Pub. Date: Mar. 14, 2002

(65) Prior Publication Data

US 2004/0136997 A1    Jul. 15, 2004

Related U.S. Application Data

(60) Provisional application No. 60/230,890, filed on Sep. 5, 2000, provisional application No. 60/229,785, filed on Sep. 1, 2000.

(51) Int. Cl.
*C07K 16/00* (2006.01)
*C12P 21/08* (2006.01)

(52) U.S. Cl. .............. 530/387.1; 530/387.3; 530/388.1; 530/388.8

(58) Field of Classification Search .................. None
See application file for complete search history.

(56) References Cited

U.S. PATENT DOCUMENTS

| | | | |
|---|---|---|---|
| 4,376,110 | A | 3/1983 | David et al. |
| 4,579,827 | A | 4/1986 | Sakamoto et al. |
| 4,713,352 | A | 12/1987 | Bander et al. |
| 4,737,579 | A | 4/1988 | Hellstrom et al. |
| 4,753,894 | A | 6/1988 | Frankel et al. |
| 4,916,055 | A * | 4/1990 | Yeoman et al. .............. 435/7.9 |
| 4,946,778 | A | 8/1990 | Ladner et al. |
| 5,212,085 | A | 5/1993 | Wands et al. |
| 5,585,089 | A | 12/1996 | Queen et al. |
| 5,595,898 | A | 1/1997 | Robinson et al. |
| 5,665,848 | A | 9/1997 | Barnard |
| 5,688,657 | A | 11/1997 | Tsang et al. |

FOREIGN PATENT DOCUMENTS

| | | |
|---|---|---|
| EP | 0155172 | 9/1985 |
| EP | 0184906 | 6/1986 |
| EP | 0252769 | 1/1988 |
| EP | 0526888 | 2/1993 |
| WO | 92/22324 | 12/1992 |
| WO | 95/03828 | 2/1995 |
| WO | 01/05427 | 1/2001 |
| WO | 02/074251 | 9/2002 |

OTHER PUBLICATIONS

Drexler et al (Leukemia and Lymphoma, 1993, 9:1-25).*
Hsu (in Tissue Culture Methods and Applications, Kruse and Patterson, Eds, 1973, Academic Press, NY, see abstract, p. 764).*
Embleton et al (Immunol Ser, 1984, 23:181-207).*
Kaiser (Science, 2006, 313:1370).*
Weiner (Seminars Oncology, vol. 26, No. 4, 1999, pp. 41-50).*
Internal Medicine, 4th Edition, Editor-in-chief Jay Stein, (Elsevier Science, 1998 Chapters 71-72, pp. 699-715).*
Kimmel et al (J. Neurosurg, 66:161-171, 1987).*
White et al. (2001, Ann. Rev. Med., 2001, 52:125-145).*
Christiansen et al (Mol Cancer Ther, 2004, 3:1493-1501).*
Topp et al (Journal of Controlled Release, 1998, 53:15-23).*
Gura (Science, 1997, 278:1041-1042).*
*Pancreas Cancer Web*, hosted at URL: http://www.path.jhu.edu/pancreas/, Copyright © 2006 The Johns Hopkins University, Baltimore, Maryland, Last Modified: May 12, 2006.
Arlen, Myron et al. (2001) "The Identification And Development Of Specific Monclonal Antibodies To Squamous Cell Carcinoma." *Critical Reviews In Immunology.* 21(1-3):205-214.
Arlen et al. (2001) Abstract #P74 entitled "Development of a therapeutic monoclonal antibody against high grade recurrent colon and pancreatic cancer." Presented at the 54th Annual Cancer Symposium, Society of Surgical Oncology, Mar. 15-18, 2001. Washington D.C.

(Continued)

*Primary Examiner*—Karen A Canella
*Assistant Examiner*—Peter J Reddig
(74) *Attorney, Agent, or Firm*—Nixon Peabody, LLP

(57) ABSTRACT

The present invention relates to novel antibodies, antibody fragments and antibody conjugates which display a high degree of selectivity for squamous cell carcinoma antigens including carcinomas of the lung, esophagus and cervix. The present invention relates to both in vivo and in vitro clinical screening methods for diagnosis or prognosis of carcinomas by means of detecting the expression of squamous cell carcinoma antigens in biological samples of the subject using the novel antibodies of the invention. The invention further provides for kits for carrying out the above described screening methods. Additionally, antibody conjugates may be used to efficiently deliver various agents which have anti-tumor effects to the tumor cell. The antibodies of the invention may also be administered to a patient in non-conjugated form to target ADCC to the tumor cell.

7 Claims, 13 Drawing Sheets

OTHER PUBLICATIONS

Figure 1:
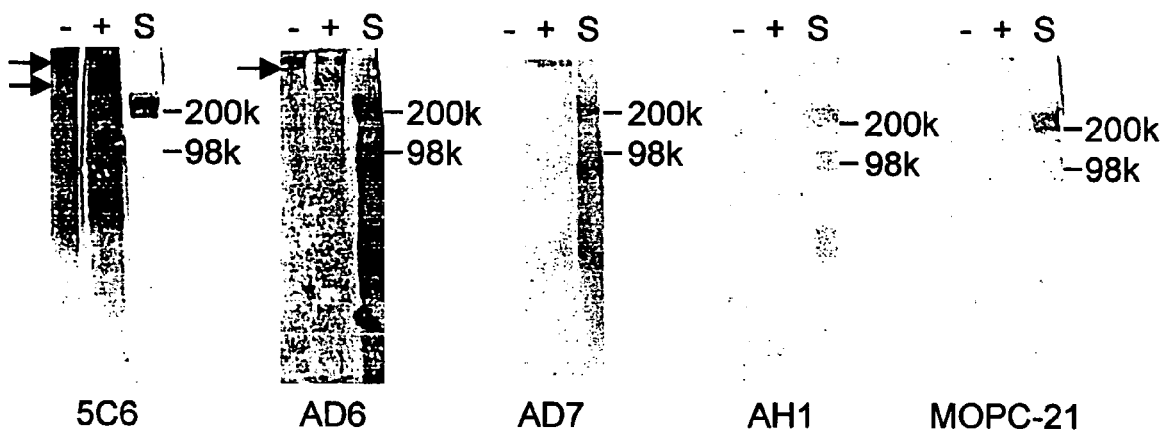

Lee et al. (1999) "Generation and characterization of a novel single-gene-encoded single-chain immunoglobulin molecule with antigen binding activity and effector functions." Mol Immunol. 36(1):61-71.

Nadkarni, Jagdish S. et al. (1998) "Characterization Of A Murine Monoclonal Antibody Against Human Esophageal Squamous Cell Carcinoma-Associated Antigen." Tumori. 84(5):578-582.

Nakao et al. (1997) "Clinical application of a new monoclonal antibody (19B7) against PIVKA-II in the diagnosis of hepatocellular carcinoma and pancreatobiliary malignancies." Am J Gastroenterol. 92(6): 1031-1034.

Simons et al. (1997) "Bioactivity of autologous irradiated renal cell carcinoma vaccines generated by ex vivo granulocyte-macrophage colony-stimulating factor gene transfer." Cancer Res. 57(8): 1537-46.

Yamada et al. (1996) "Aberrant Expression Of A Hemidesmosomal Protein, Bullous Pemphigold Antigen 2, In Human Squamous Cell Carcinoma." Laboratory Investigation 75(4): 589-600.

Sung et al. (1995) "Natural killer (NK) cells as effectors of antibody-dependent cytotoxicity with chimeric antibodies reactive with human squamous-cell carcinomas of the head and neck." Int J Cancer. 61(6): 864-872.

Bird et al. (1988) "Single-Chain Antigen-Binding Proteins." Science 242: 423-426.

* cited by examiner

NORMAL LUNG

10 X Magnification　　　　　　　　　　　　Probed with AD6

NORMAL LUNG

4 X Magnification　　　　　　　　　　　　Probed with AD7

SCC Lung Lavage

40 X Magnification　　　　　　　　　　　Probed with AD6

SCC Lung Lavage

20 X Magnification　　　　　　　　　　　Probed with 5C6

SCC Lung

20 X Magnification  Probed with 5C6

SCC Lung

10 X Magnification  Probed with AD6

Pap Smear Technology utilizing immunohistochemistry with specific Squamous Cancer antibodies, 5C6 and AD7

Thin prep technology for cervical cancer. Slide represents dysplasia but indicates presence of cell genotypically presenting cancer antigen.

Squamous Carcinoma of the Cervix

In situ-carcinoma
Immunoperoxidase
Using C56 ->
(Top)

Invasive squamous carcinoma of cervix staining with AD7
(Bottom)

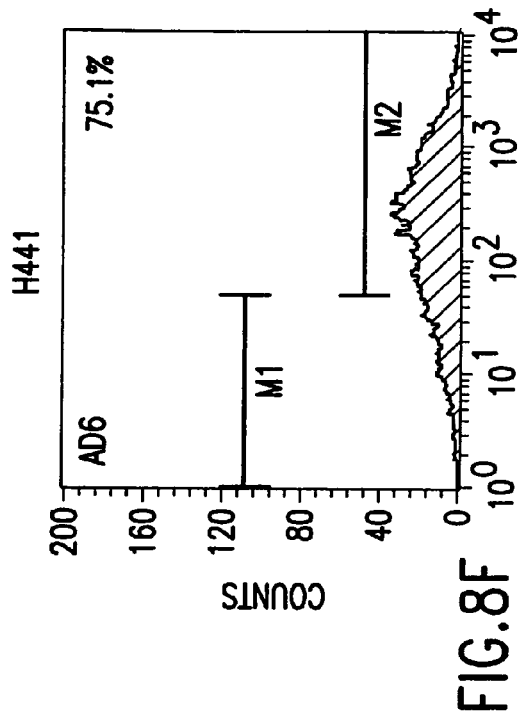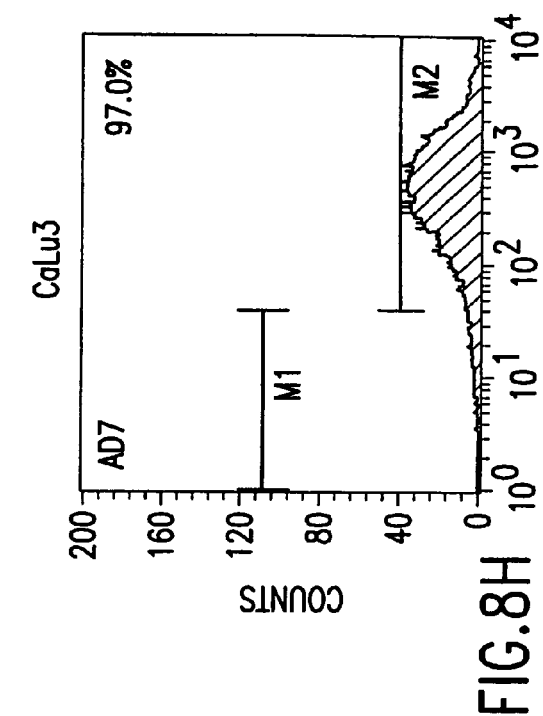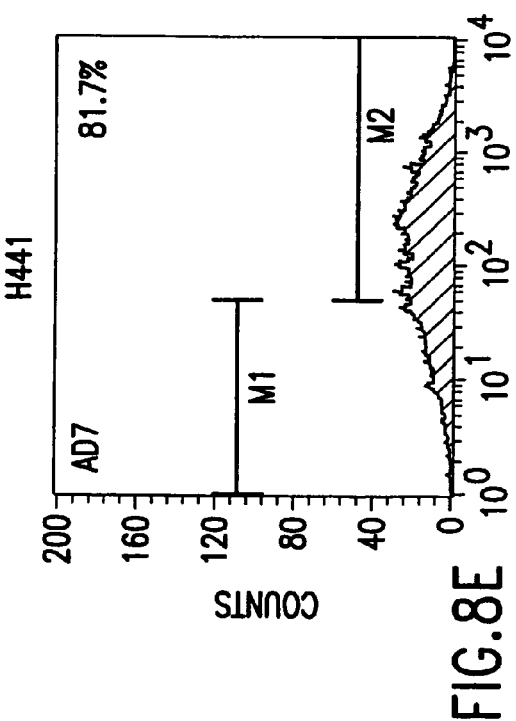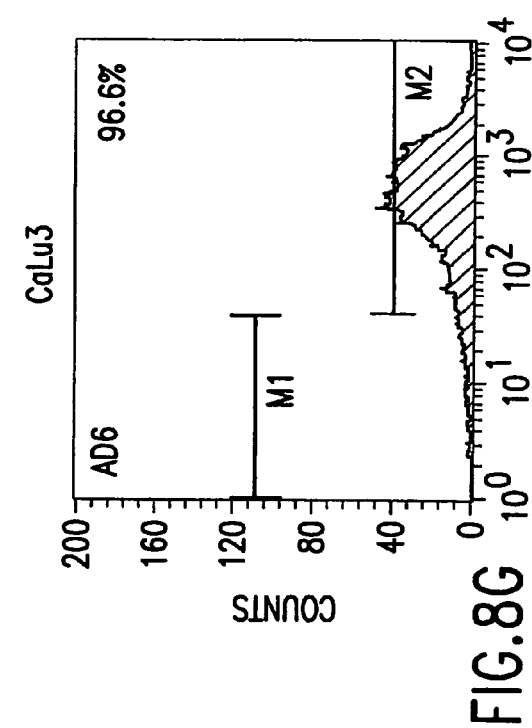

IDENTIFICATION AND DEVELOPMENT OF SPECIFIC MONOCLONAL ANTIBODIES TO SQUAMOUS CELL CARCINOMA

This application is a 371 of PCT/US01/26734 filed Aug. 28, 2001, which claims benefit of 60/229,785 filed Sep. 1, 2000, and claims benefit of 60/230,890, filed Sep. 5, 2000.

SEQUENCE LISTING

The specification further incorporates by reference the Sequence Listing submitted herewith via EFS on Jan. 2, 2008. Pursuant to 37 C.F.R. § 1.52(e)(5), the Sequence Listing text file, identified as 072771.0112.SEQLIST.TXT, is 1,464 bytes and was created on Dec. 29, 2007. The Sequence Listing, electronically filed herewith, does not extend beyond the scope of the specification and thus does not contain new matter.

1. INTRODUCTION

The present invention relates to novel antibodies, antibody fragments and antibody conjugates which display a high degree of selectivity for squamous cell carcinoma antigens including carcinomas of the lung, esophagus and cervix. The present invention relates to both in vivo and in vitro clinical screening methods for diagnosis or prognosis of carcinomas by means of detecting the expression of squamous cell carcinoma antigens in biological samples of the subject using the novel antibodies of the invention. The invention further provides for kits for carrying out the above described screening methods. Such kits can be used to screen subjects for expression of squamous cell carcinoma antigens as a diagnostic, predictive or prognostic indicator of cancer. Additionally, antibody conjugates may be used to efficiently deliver various agents which have anti-tumor effects including, but not limited to, chemotherapeutic drugs, toxins, immunological response modifiers, and radioisotopes, immunological response modifiers may also be provided in the form of fusion proteins. Immunological response modifiers may also be provided in the form of fusion proteins and radioisotopes may also be delivered while conjugated to single chain Fv chain constructs. The antibodies of the invention may also be administered to a patient in unconjugated form to target ADCC to the tumor cell.

2. BACKGROUND OF INVENTION

Lung cancer is one of the more common malignancy effecting the population. Once a tumor is diagnosed, the overall prognosis is poor, with an overall five year survival rate of only 13%. However, early detection and treatment of lung cancer can significantly improve 5 year survival rates. In those cases where the disease is detected early and surgical resection is feasible, the five year survival rate increases to 40%. For those at high risk for development of lung cancer intensive monitoring has not been effective in reducing the incidence of the disease or its outcome due in part to the inability to define early stages of the disease when transformation is first occurring within normal cell populations of the tracheobronchial tree.

Monoclonal antibodies to tumor-associated antigens provide useful reagents for diagnosis of cancer and for targeting of various anti-tumor agents such as radioisotopes, chemotherapeutic drugs and toxins to the site of the tumor. Many monoclonal antibodies reactive against carcinoma-associated antigens are known. These known antibodies bind to a variety of different carcinoma-associated antigens that include glycoproteins but for the most part bind to the carbohydrate moiety. For example, monoclonal antibodies that bind to glycoprotein antigens on specific types of carcinomas include those described in U.S. Pat. Nos. 4,737,579; 4,753,894; 4,579,827 and 4,713,352.

Since many tumor cells shed their membrane glycoproteins into surrounding body fluids such as serum, or bronchial secretions in the case of squamous cell carcinomas, the possibility of detecting shed antigen using monoclonal antibodies in an ELISA is a possible approach to early detection. This is the approach taken for detection of tumor markers such as PSA and CEA in serum. As an example, supernatants of the bronchial lavage could be used in immunoassays designed for early detection of transformed cells in bronchial epithelium where shed antigen appears in the supernatant fluid. To date, assays designed to define tumor cells in sputum samples have proven to be ineffective because of the unavailability of monoclonal antibodies capable of differentiating between normal and abnormal squamous cells or to be able to define genotypically altered cells before the phenotypic changes of malignancy are evident.

Most studies have employed epithelial markers such as cytokeratin antibodies which are non-specific and will react with most if not all epithelial cells. Thus, better monoclonal antibody based diagnostic and prognostic markers and more sensitive tests for use in defining clinical lung cancer are needed. Ideally the monoclonal antibodies will detect the expression of a specific tumor antigen at an early time when clinical disease is not obvious. Such a tumor antigen defined by a monoclonal antibody could be used as a target for immunotherapy directed against the specific tumor antigen expressed on the surface of the cell. Such antibodies may also be of prognostic value based their ability to identify markers expressed at different stages of disease or that function differently, i.e., e-capherin, growth factor or receptor.

3. SUMMARY OF THE INVENTION

The present invention relates to monoclonal antibodies, antibody fragments, and antibody conjugates that are highly selective for squamous cell carcinomas. More specifically, the novel antibodies, antibody fragments and antibody conjugates of the invention are those that bind to a cell membrane antigen found on squamous cell carcinomas but show no or limited reactivity with normal cells or other types of cancers. The invention also relates to hybridoma cell lines that produce monoclonal antibodies that are highly selective for squamous cell carcinomas.

In yet another embodiment of the invention, the antibodies of the invention may be used for in vitro or in vivo diagnostic and prognostic methods designed to detect squamous cell carcinoma. For instance, the antibody may be used in methods designed to detect the presence of a malignant condition in human lung, cervical or other tissue. The tissue may be contacted with an antibody of the invention which is capable of distinguishing squamous cell carcinoma cells from other cell types which may be present in the sample. Contact is carried out under conditions that allow for binding of the antibody to such cells followed by detecting the presence or absence of binding of the antibody to the cells of the specimen. Additional diagnostic methods include the in vivo localization of a tumor by administering to a patient a purified antibody or antibody fragment of the present invention labeled with an agent which gives a detectable signal. The localization of the tumor is then detected using external scintography, emission tomography or radionuclear scanning.

The invention further relates to the use of the antibodies of the invention in therapeutic applications, for example, to react with targeted tumor cells. For example, novel antibody conjugates that act as target selective carriers of various agents which have antitumor effects including chemotherapeutic drugs, toxins, immunological response modifiers, enzymes and radioisotopes can be used.

Alternatively, the monoclonal antibodies may be used even in unmodified, i.e., not in conjugated form, to treat subjects having squamous cell carcinoma. The antibodies of the present invention are particularly well suited for mediating antibody dependent cellular cytotoxicity (ADCC) which can results in targeted lysis of carcinoma cells in the presence of human lymphocytes, macrophages and complement.

The invention also comprises the antigens identified by the antibodies of the invention. Further encompassed are methods for using the purified or cloned antigens defined by the antibodies as vaccines to immunize against certain squamous cell carcinomas.

4. BRIEF DESCRIPTION OF THE FIGURES

FIG. 1. Western Blot of Lung Lavage with Monoclonal Antibodies 5C6, AD6, AD7, and AH1.

Figure 2:
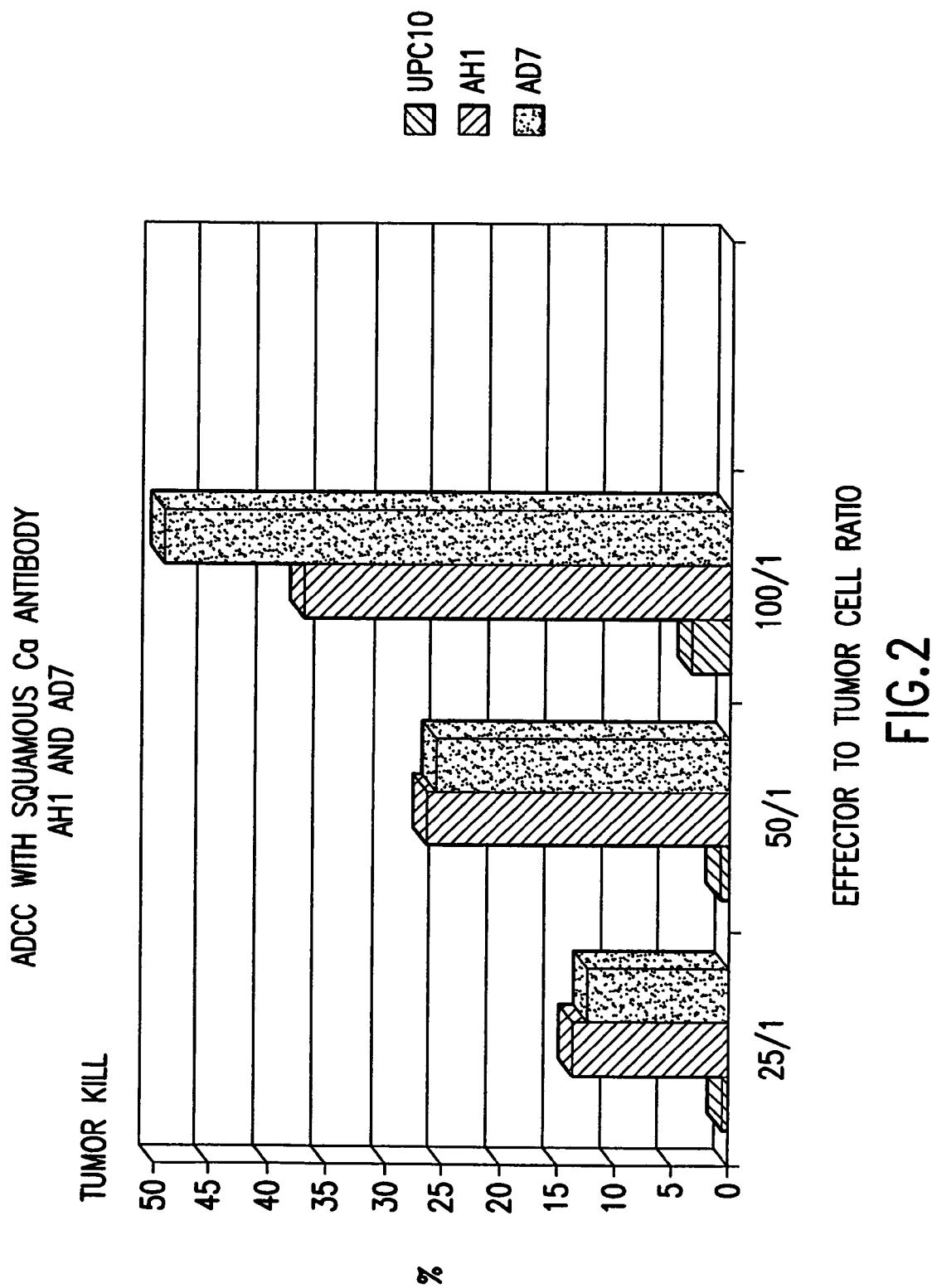

FIG. 2. ADCC With Squamous Cell Carcinoma Specific Antibodies AH1 and AD7 and control antibody UPC-10.

Figure 3A:
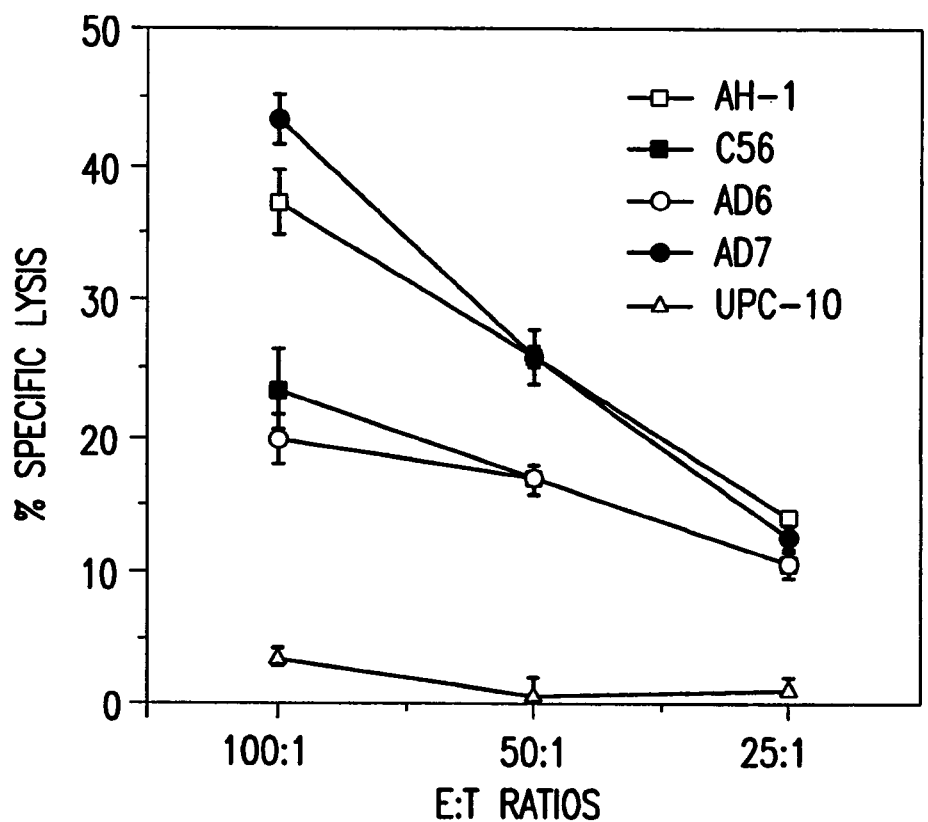

FIG. 3A. ADCC With Squamous Cell Carcinoma Specific Antibodies AH1, AD6, AD7, 5C6 and control antibody UPC-10 against human squamous cell carcinoma cell line H596.

Figure 3B:
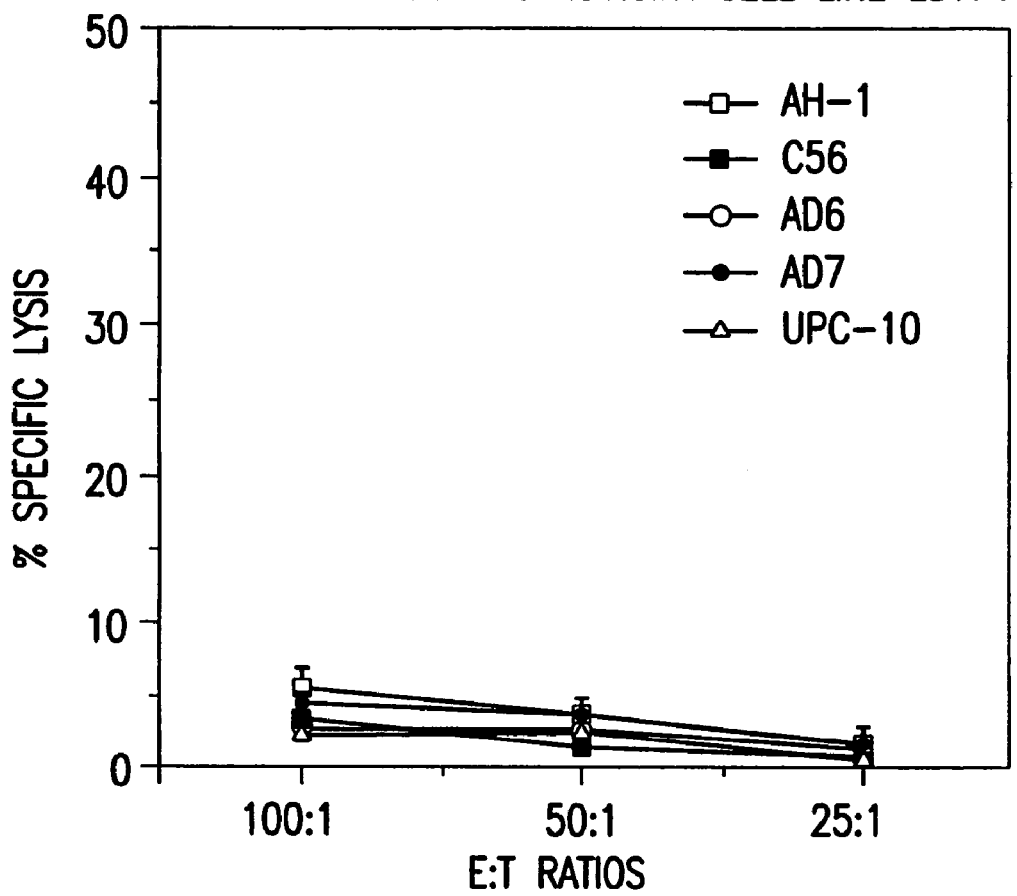

FIG. 3B. ADCC With Squamous Cell Carcinoma Specific Antibodies AH1, AD6, AD7, 5C6 and control antibody UPC-10 against human colon carcinoma cell line LS174T.

Figure 4A:
Figure 4B:
Figure 4C:
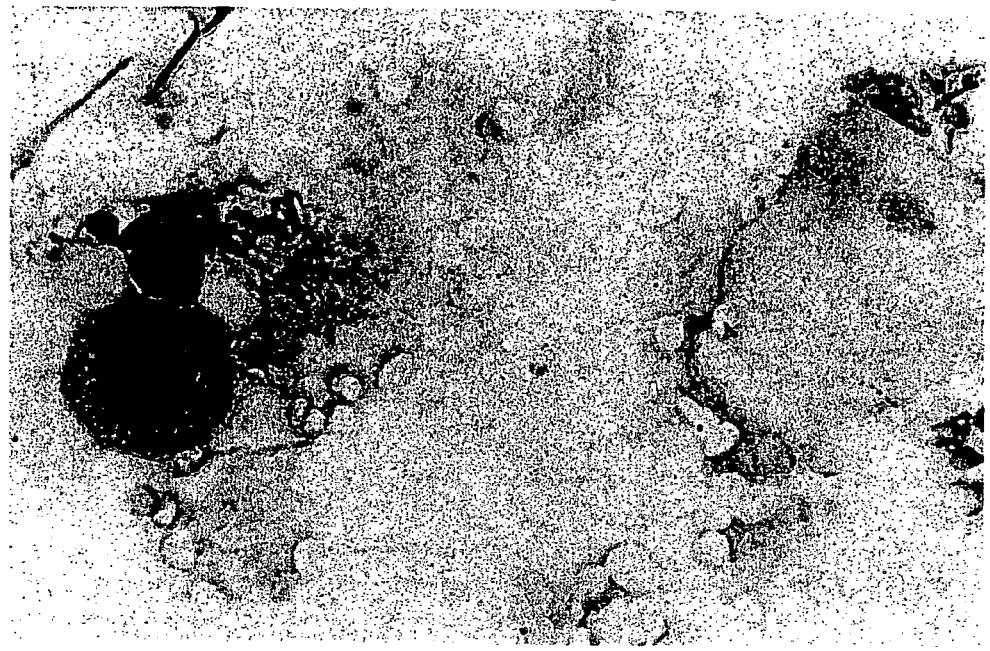
Figure 4D:
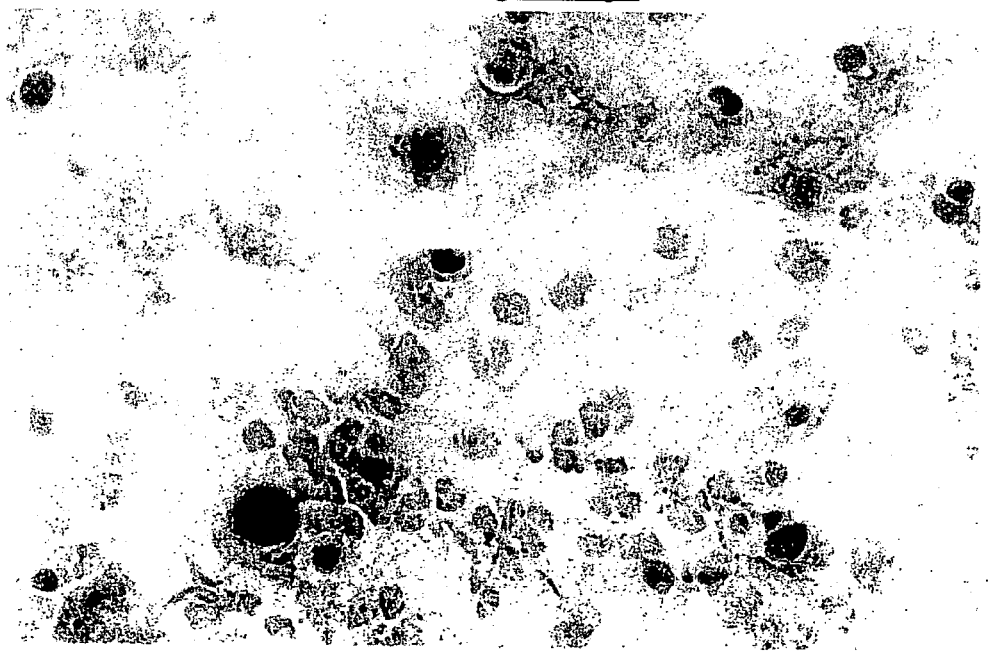
Figure 4E:
Figure 4F:
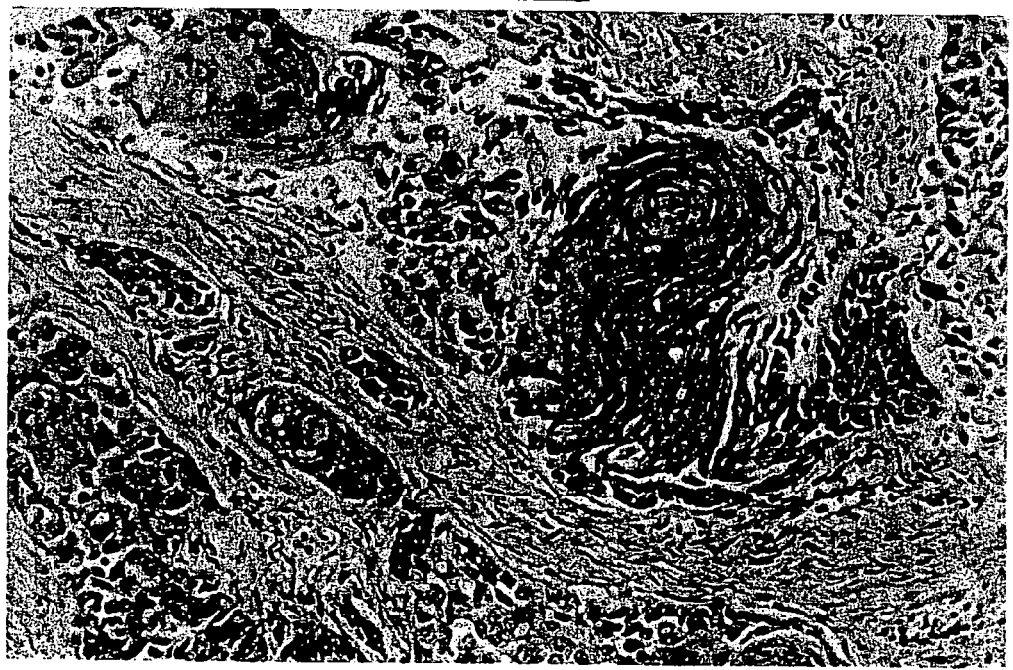

FIGS. 4A-F. Immunohistology Using Squamous Cell Carcinoma Specific Antibodies AH6, AD7, and 5C6. FIG. 4A. Normal Lung Tissue probed with AD6. FIG. 4B. Normal Lung Tissue probed with AD7. FIG. 4C. Squamous Cell Carcinoma Lung Lavage probed with AD6. FIG. 4D. Squamous Cell Carcinoma Lung Lavage probed with 5C6. FIG. 4E. Squamous Cell Carcinoma probed with 5C6. FIG. 4F. Squamous Cell Carcinoma probed with AD6.

Figure 5:
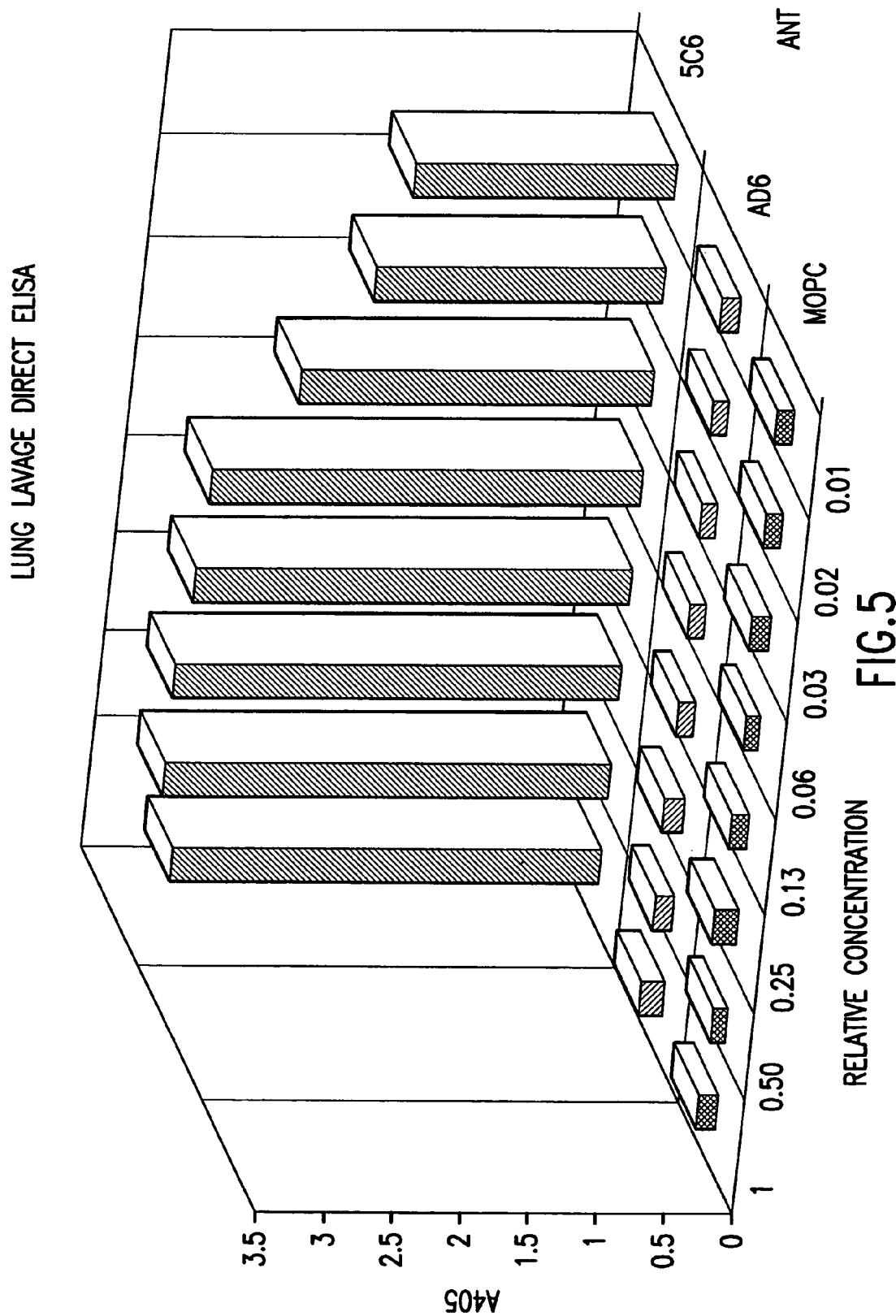

FIG. 5. Direct ELISA assay with 5C6 and AD6 monoclonal antibodies using lung lavage sample.

Figure 6:
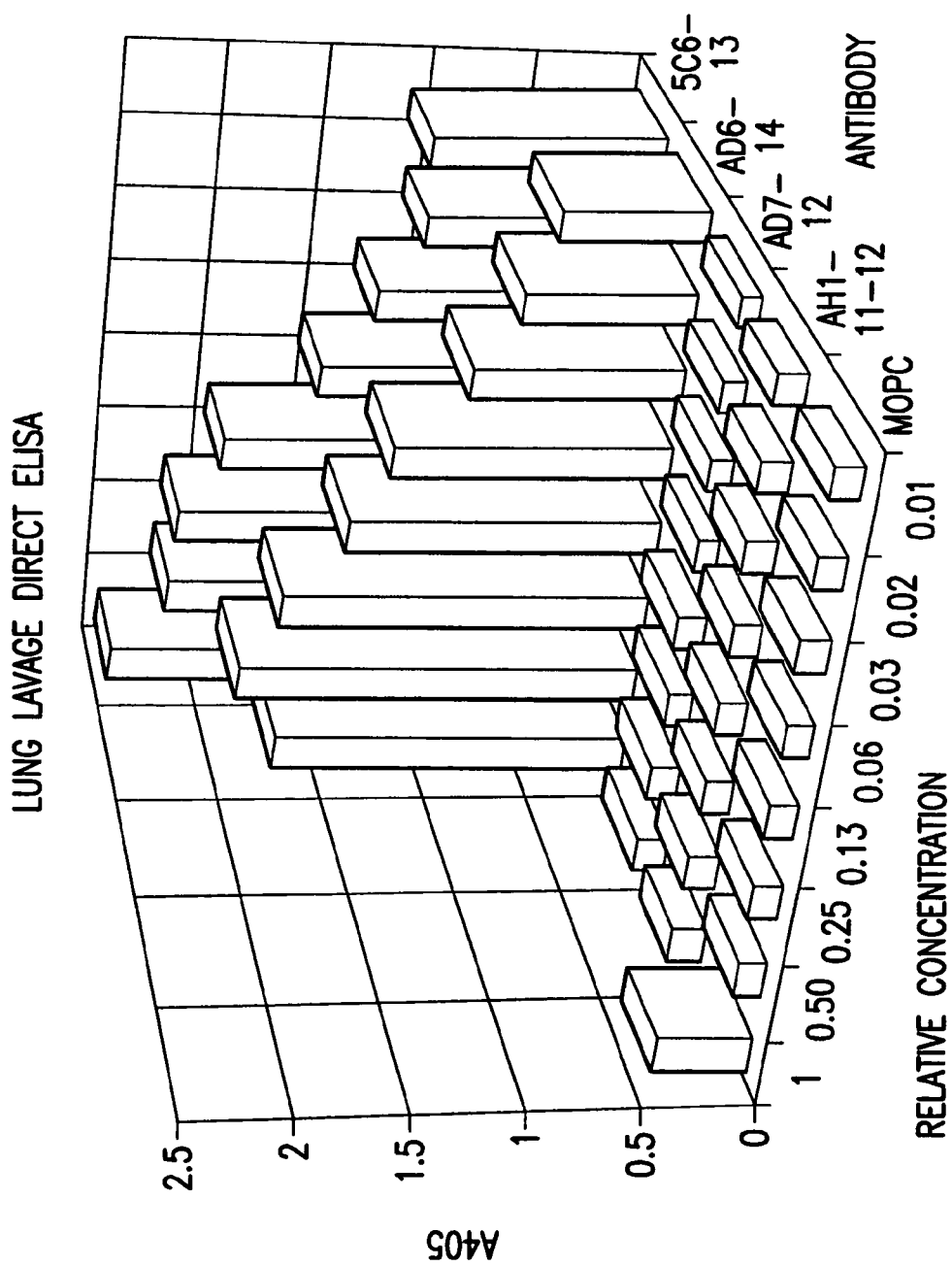

FIG. 6. Direct ELISA assay with 5C6, AD6, AH1 and AD7 monoclonal antibodies using lung lavage sample.

Figure 7A:
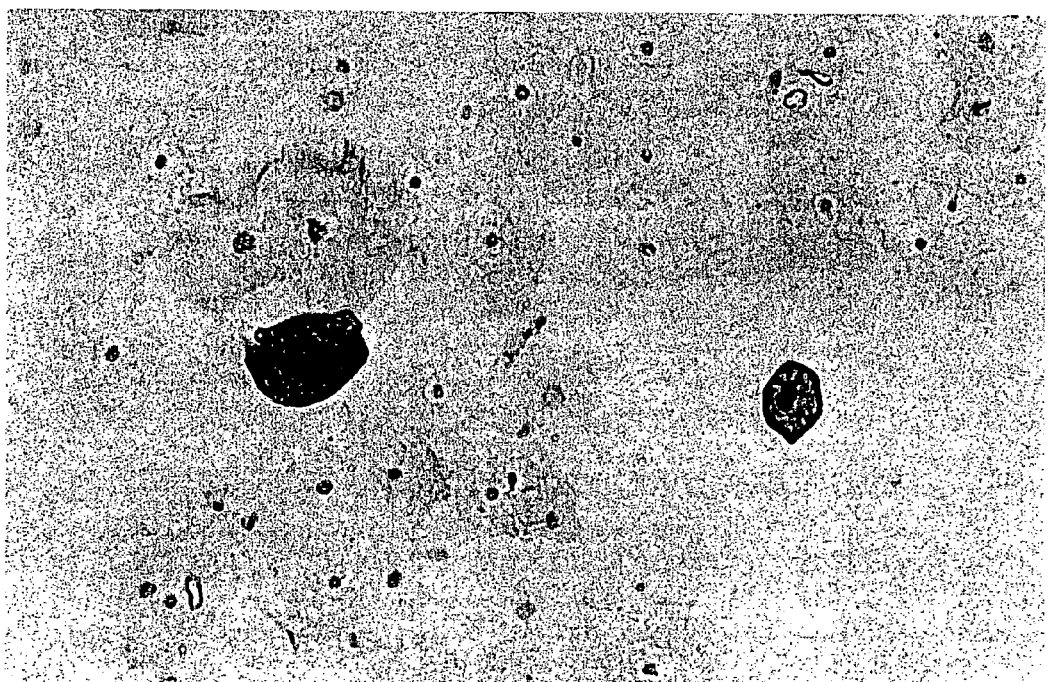

FIG. 7A. Pap Smear using 5C6 and AD7 monoclonal antibodies. Slide represents dysplasia but indicates the presence of cell expressing carcinoma specific antigens.

Figure 7B:
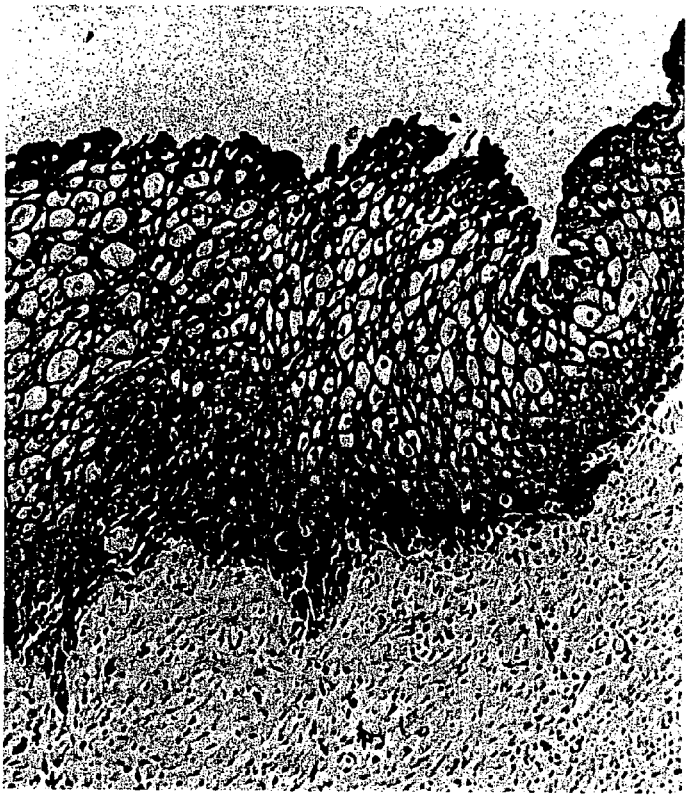
Figure 7B:
Figure 8B:
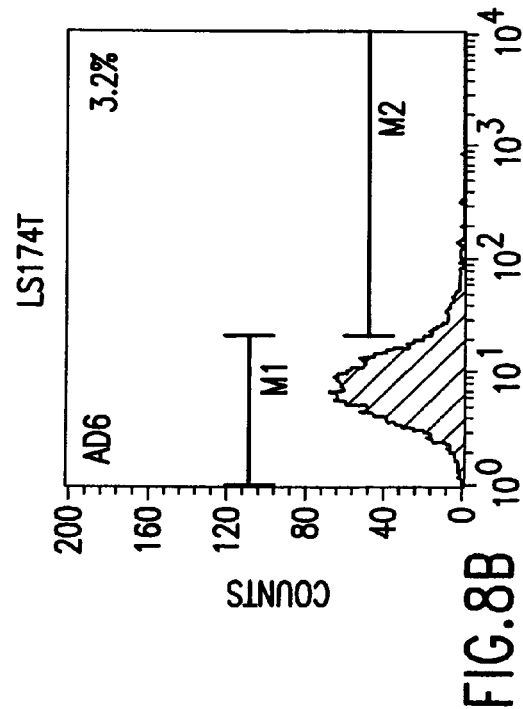
Figure 8D:
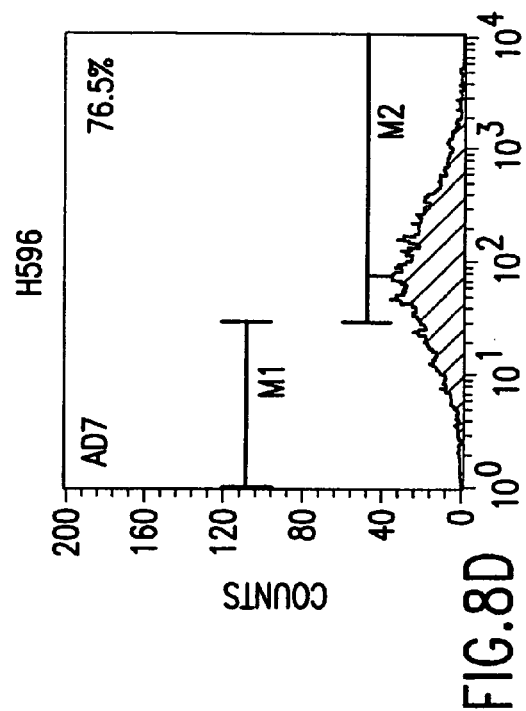
Figure 8A:
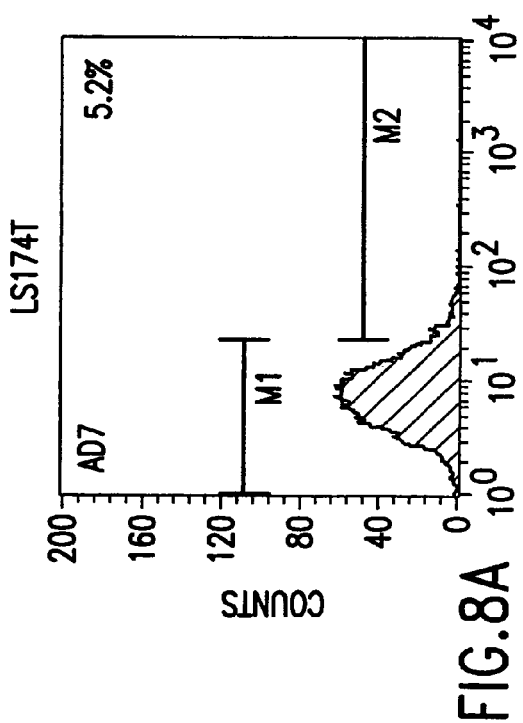
Figure 8C:
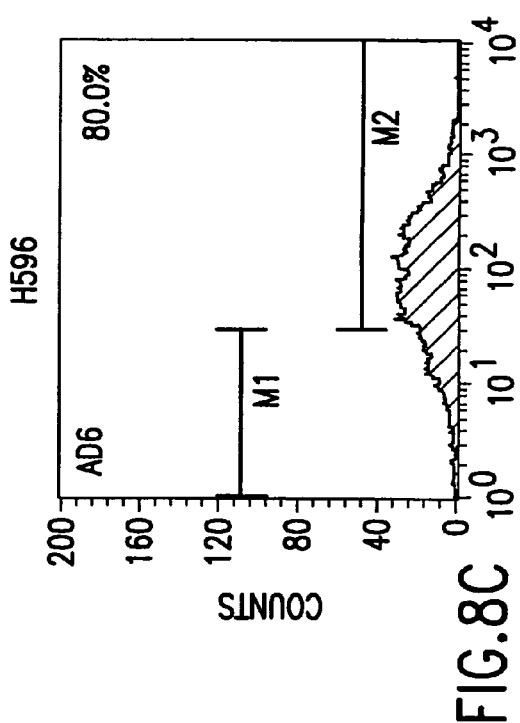

FIG. 7B. In situ immunoperoxidase staining of cervical carcinoma cells using C56 (top) and AD7 (bottom).

FIGS. 8A, 8D 8E and 8H. LS174T colon carcinoma cells, H596 cells, H441 cells and CaLu3 lung carcinoma cells stained with the AD7 antibody.

FIGS. 8B, 8C, 8F and 8G. LS174T colon carcinoma cells, H596 cells, H441 cells and CaLu3 lung carcinoma cells stained with the AD6 antibody.

5. DETAILED DESCRIPTION OF THE INVENTION

The present invention relates to novel monoclonal antibodies that are highly specific for squamous cell carcinomas. More specifically, the antibodies react with squamous cell carcinoma of the lung and cervix, while showing none or limited reactivity with normal tissue. Such antibodies include those designated AD6, 5C6, AD7, and AH1. All four antibodies were reactive to lung cancer antigen and to human lung cancer cell lines when assayed using ELIZA and immunofluorescent assays. In addition, the antibodies exhibit strong ADCC and immunohistochemical activity.

5.1 Squamous Cell Carcinoma Specific Antibodies

The present invention relates to novel antibodies that are highly specific for squamous cell carcinoma cells of the lung and cervix while showing none or limited reactivity with normal human tissue. The novel antibodies of the invention are designated AD6, 5C6, AD7, and AH1. The designated antibodies can be used to isolate and characterize the antigen to which they bind. Thus, the antibodies can be used to identify, isolate and/or characterize the immunogenic cell surface glycoproteins to which they react.

The term "AD6 antibody" as used herein includes whole, intact polyclonal and monoclonal antibodies such as the murine AD6 monoclonal antibody produced by hybridoma ATCC No. PTA-2460, and chimeric antibody molecules capable of binding to the same antigenic determinant as the AD6 antibody. The AD6 antibody described above includes fragments thereof containing the active antigen-binding region of the antibody, including Fab, F(ab'), and Fv fragments. The AD6 antibody of the invention also includes fusion proteins.

The term "5C6 antibody" as used herein includes whole, intact polyclonal and monoclonal antibodies such as the murine 5C6 monoclonal antibody produced by hybridoma ATCC No. PTA-2458 (deposited on Sep. 6, 2000 with the American Type Culture Collection at 10801 University Blvd., Mass., VA 20110-2209 under the Budapest Treaty on the International Recognition of the Deposit of Microorganisms for the Purposes of Patent Procedure), and chimeric antibody molecules capable of binding to the same antigenic determinant as the 5C6 antibody. The 5C6 antibody described above includes fragments thereof containing the active antigen-binding region of the antibody, including Fab, F(ab'), and Fv fragments. The 5C6 antibody of the invention also includes fusion proteins.

The term "AD7 antibody" as used herein includes whole, intact polyclonal and monoclonal antibodies such as the murine AD7 monoclonal antibody produced by hybridoma ATCC No. PTA-2459, and chimeric antibody molecules capable of binding to the same antigenic determinant as the AD7 antibody. The AD7 antibody described above includes fragments thereof containing the active antigen-binding region of the antibody, including Fab, F(ab'), and Fv fragments. The AD7 antibody of the invention also includes fusion proteins.

The term "AH1 antibody" as used herein includes whole, intact polyclonal and monoclonal antibodies such as the murine AH1 monoclonal antibody produced by hybridoma ATCC No. PTA-2457, and chimeric antibody molecules capable of binding to the same antigenic determinant as the AH1 antibody. The AH1 antibody described above includes fragments thereof containing the active antigen-binding region of the antibody, including Fab, F(ab'), and Fv fragments. The AH1 antibody of the invention also includes fusion proteins.

The present invention further encompasses the hybridoma cell lines capable of producing antibodies specific for squamous cell carcinoma cell surface antigens. Such hybridoma cell lines include but are not limited to hybridoma ATCC No. PTA-2457, hybridoma ATCC No. PTA-2459, hybridoma ATCC No. PTA-2458, and hybridoma ATCC No. PTA-2460.

Murine hybridomas which produce mAB specific for squamous cell carcinoma cell surface antigens, such as the AD6, 5C6, AD7 and AH1 antibodies of the present invention, are formed by the fusion of a mouse fusion partner cell, such as SP2/0 and spleen cells isolated from mice immunized with squamous cell carcinoma cell surface antigens. Mice may be immunized with crude or semi-purified preparations containing the antigens of interest. To immunize mice, a variety of different conventional protocols may be followed. For example, mice may receive primary and boosting immunizations of antigenic preparations.

The monoclonal antibodies of the invention may be obtained by any technique which provides for the production of antibody molecules by continuous cell lines in culture. These include, but are not limited to, the hybridoma technique of Kohler and Milstein, (1975, Nature 256:495-497; and U.S. Pat. No. 4,376,110), the human B-cell hybridoma technique (Kosbor et al., 1983, Immunology Today 4:72; Cole et al., 1983, Proc. NatL Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclasses thereof. The hybridoma producing the mAb of this invention may be cultivated in vitro or in vivo. Production of high titres of Mabs in vivo makes this the presently preferred method of production.

In addition, techniques developed for the production of "chimeric antibodies" by splicing the genes from a mouse antibody molecule of appropriate antigen specificity together with genes from a human antibody molecule of appropriate biological activity can be used (Morrison et al., 1984, Proc. Nat'l. Acad. Sci., 81:6851-6855; Neuberger et al., 1984, Nature, 312: 604-608; Takeda et al. 1985, Nature 314: 452-454). Chimeric antibodies may be produced using a two-step homologous recombination procedure such as that described in Fell et al., (1989, Proc. Nat'l. Acad. Sci., 86:8507-8511). Alternatively, techniques developed for the production of humanized antibodies (U.S. Pat. No. 5,585,089) or single chain antibodies (U.S. Pat. No. 4,946,778 Bird, 1988, Science 242: 423-426; Huston et al., 1988, Proc. Nat'l. Acad. Sci USA, 85: 5879-5883; and Ward et al., 1989, Nature 334: 544-546) may be used to produce antibodies that specifically recognize squamous carcinoma.

The monoclonal antibodies of the invention may be produced in large quantities by injecting hybridoma cells secreting the antibody into the peritoneal cavity of mice and, after an appropriate time, harvesting the ascites fluid which contains a high titre of the monoclonal antibody and isolating the antibody therefrom. The monoclonal antibodies may be produced by culturing hybridoma cells in vitro and isolating the secreted mAB from the cell culture medium (See, Cole et al., 1985, in Monoclonal Antibodies and Cancer Therapy, Alan R. Liss, Inc.). Alternatively, the gene for the antibody can be placed into a viral vector and used as a form of gene therapy so that the patient receiving the antibody gene can produce therapeutic antibody through his own immune system.

In addition, antibody fragments including fragments thereof containing the active antigen-binding region of the antibody may be prepared using techniques well established in the art (see, for example, 1986, Methods in Enzymology 121:663-69(Academic Press)).

Also included within the scope of the invention are anti-idiotypic antibodies to the AD6, 5C6, AD7 and AH1 antibodies of the invention. The anti-idiotypic antibodies can be produced using the AD6, 5C6, AD7 and AH1 antibodies and/or fragments thereof as immunogens. Such anti-idiotypic antibodies are useful as diagnostic reagents for detecting a humoral response to tumors and in therapeutic applications such as in a vaccine, to induce an anti-tumor response in subjects with squamous cell carcinomas.

Chimeric antibodies having the same binding specificity as the AD6, 5C6, AD7 and/or AH1 antibodies and combined with a cytotoxic agent are encompassed by the present invention. Such immunotoxins can be generated using genetic engineering techniques known in the art to produce recombinant DNA molecules capable of encoding a fusion protein containing the antigen binding region of the AD6, 5C6, AD7 or AH1 monoclonal antibody fused to a cytotoxic agent such as, for example, diptheria toxin. In addition, humanized or completely human antibodies can be produced using recombinant engineering techniques resulting in production of antibodies that induce less of an anti-mouse response.

The present invention encompasses novel antibody conjugates that act as target selective carriers of various agents which have anti-tumor effects including chemotherapeutic drugs, toxins, immunological response modifiers, enzymes and radioisotopes can be used. Such agents may be conjugated to the monoclonal antibodies of the invention for use in targeting the agent to the surface of squamous cell carcinoma cells. Such cytotoxic agents include for example vinca alkaloids, ricin, taxol, doxorubicin, methotrexate, mitomycin C, and cytochalasin B to name a few. Immunological response modifiers may also be provided in the form of fusion proteins and radioisotopes may also be delivered while conjugated to single chain Fv chain constructs.

To generate the specific antibodies of the present invention, immunogenic glycoproteins derived from squamous cell carcinomas of the lung were isolated. The antigen was prepared from pooled allogeneic material sampled at the time of surgery and fractionated by Sephadex G-200 chromatography. Balb/c mice were immunized with the partially purified soluble membrane antigens of the human lung carcinoma cells and, after a sufficient time, the mice were sacrificed and somatic antibody producing lymphocytes, e.g., spleen cells, were obtained and fused with the murine myeloma cell line SP2/0-Ag14.

Following fusion, the resulting cells were allowed to grow in selective medium, such as HAT-medium, and the surviving cells are grown in such medium using limiting dilution conditions and the supernatant was screened for monoclonal antibodies having the desired specificity. Various conventional methods exist for isolation and purification of the monoclonal antibodies, so as to free them from other proteins and other contaminants.

Four hybrid clones were found to produce antibodies with the desired specificity. These antibodies were designated as AD6, 5C6, AD7, and AH1. All four monoclonal antibodies were found to reactive to lung cancer antigen and to human lung cancer cell lines as assayed by ELISA and immunofluorescent assays. The antibodies did not react with normal tissue, bone marrow or tumor cell lines of other histological types. In addition, western blot analysis was performed using protein extracts derived from lung carcinoma cell lines P3 and P6 and partially purified lung cancer membrane antigens. Antigens of various molecular weight were detected using the four different antibodies indicating that each of the monoclonal antibodies recognized a distinct antigen expressed on the cell membrane These antibodies appear to identity biomarkers on an array of squamous cell cancers including lung, esophagus and cervix cancer. We have demonstrated that the antibodies, i.e., 5C6 and AD7 are far more sensitive in cervical squamous malignancies than commercially available antibodies. In addition, if the pap smear is performed using thin prep technology so that cells are placed into fixative, the cytospin can be used as a source for measuring and defining a tumor antigen.

5.2. Diagnostic Assays for Detection of Squamous Cell Carcinoma Specific Antigens In accordance with the invention, the squamous cell carcinoma specific monoclonal antibodies of the present invention can be used for the early diagnosis of diseases such as lung, esophagus and cervical carcinoma. Moreover, the monitoring and quantitation of antigen levels can be used prognostically to stage the progression of the disease and to evaluate the efficacy of agents used to treat a cancer subject. Antigen levels can be monitored from cytospins by direct ELISA or in serum with a capture assay.

The detection of squamous cell carcinoma specific antigens in a sample from a subject can be accomplished by any of a number of methods. Preferred diagnostic methods for the detection of squamous cell carcinoma specific antigens in the biological sample of a subject can involve, for example, immunoassays wherein the antigens are detected by their interaction with the specific antibodies of the invention. Antibodies useful in the present invention can be used to quantitatively or qualitatively detect the presence of squamous cell carcinoma specific antigens or fragments thereof. For example, the monoclonal antibodies of the invention can be used, for example, to detect carcinoma cells in histological and cytological specimens.

For instance, using an immunoperoxidase staining technique tissue specimens can be analyzed for positive staining (Garrigues et al., 1982, Int. J.Cancer 29:511). Immunoassays useful in the practice of the invention include but are not limited to assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement fixation assays, immunoradiometric assays, fluorescent immunoassays, protein A immunoassays, to name but a few.

A biological sample which may contain squamous cell carcinoma specific antigens proteins, such as lung tissue or other biological tissue, is obtained from a subject suspected of having a particular cancer or risk for cancer. Aliquots of whole tissues, or cells, are solubilized using any one of a variety of solubilization cocktails known to those skilled in the art. For example, tissue can be solubilized by addition of lysis buffer comprising (per liter) 8 M urea, 20 ml of Nonidet P-40 surfactant, 20 ml of ampholytes (pH 3.5-10), 20 ml of 2-mecaptoethanol, and 0.2 mM of phenylmethylsulfonyl fluoride (PMSF) in distilled deionized water.

Immunoassays for detecting expression of squamous cell carcinoma specific antigens typically comprise contacting the biological sample, such as a tissue sample derived from a subject, with the monoclonal antibodies of the invention, i.e., AD6, 5C6, AD7, and AH1, under conditions such that an immunospecific antigen-antibody binding reaction can occur, and detecting or measuring the amount of any immunospecific binding by the antibody. In a specific aspect, such binding of antibody, for example, can be used to detect the presence and/or increased production A biological sample which may contain squamous cell carcinoma specific antigens proteins, such as lung tissue or other biological tissue, is obtained from a subject suspected of having a particular cancer or risk for cancer. Aliquots of whole tissues, or cells, are solubilized using any one of a variety of solubilization cocktails known to those skilled in the art. For example, tissue can be solubilized by addition of lysis buffer comprising (per liter) 8 M urea, 20 ml of Nonidet P-40 surfactant, 20 ml of ampholytes (pH 3.5-10), 20 ml of 2-mecaptoethanol, and 0.2 mM of phenylmethylsulfonyl fluoride (PMSF) in distilled deionized water.

Immunoassays for detecting expression of squamous cell carcinoma specific antigens typically comprise contacting the biological sample, such as a tissue sample derived from a subject, with the monoclonal antibodies of the invention, i.e., AD6, 5C6, AD7, and AH1, under conditions such that an immunospecific antigen-antibody binding reaction can occur, and detecting or measuring the amount of any immunospecific binding by the antibody. In a specific aspect, such binding of antibody, for example, can be used to detect the presence and/or increased production of squamous cell carcinoma specific antigens wherein the detection or increased production of squamous cell carcinoma specific antigens is an indication of a diseased condition. The levels of squamous cell carcinoma specific antigens in a biological sample are compared to norms established for age and gender-matched normal individuals and for subjects with a variety of non-cancerous or pre-cancerous disease states.

In an embodiment of the invention, the biological sample, such as a tissue extract is brought in contact with a solid phase support or carrier, such as nitrocellulose, for the purpose of immobilizing any proteins present in the sample. The support is then washed with suitable buffers followed by treatment with detectably labeled monoclonal antibodies such as AD6, 5C6, AD7, and/or AH1. The solid phase support is then washed with the buffer a second time to remove unbound antibody. The amount of bound antibody on the solid support is then determined according to well known methods. antibodies or antibody fragments, it is possible to detect squamous cell carcinoma specific antigen expression through the use of a radioimmunoassay (RIA) (see, for example, Weintraub, B., *Principles of Radioimmunoassays*, Seventh Training Course on Radioligand Assay Techniques, The Endocrine Society, March 1986). The radioactive isotope can be detected by such means as the use of a gamma counter or a scintillation counter or by autoradiography.

The monoclonal antibodies may also be labeled with a fluorescent compound. Among the most commonly used fluorescent labeling compounds are fluorescein isothiocyanate, rhodamine, phycoerythrin and fluorescamine. Likewise, a bioluminescent compound may be used to label the monoclonal antibodies. The presence of a bioluminescence protein is determined by detecting the presence of luminescence. Important bioluminescence compounds for purposes of labeling are luciferin, luciferase and aequorin.

The antibodies of the invention can also be employed for in vivo diagnostic applications. For example, antibodies or fragments prepared from antibodies, can be used to image tumors, including metastatic tumors in human patients. The purified antibody or fragments thereof are labeled with an agent capable of giving a detectable signal and administered in a suitable carrier, for example, intravenously, to a patient. The localization of the tumor-bound antibody is detected by external scintography, emission tomography or radionuclear scanning, using for example, a gamma camera.

5.3. Kits

The present invention further provides for kits for carrying out the above-described assays. The assays described herein can be performed, for example, by utilizing pre-packaged diagnostic kits, comprising at an antibody reagent (for detection of squamous cell carcinoma specific antigens), which can be conveniently used, e.g., in clinical settings to diagnose disorders such as cancer. Such antibody reagents include the monoclonal antibodies AD6, 5C6, AD7, and AH1.

In a nonlimiting embodiment, a kit according to the invention may comprise components which detect and/or measure squamous cell carcinoma specific antigens in the biological sample of a subject. For example, where squamous cell carcinoma specific antigens are detected and/or measured by enzyme linked immunoabsorbent assay (ELISA), such components may comprise an antibody directed to epitopes of the squamous cell carcinoma specific antigens which can be used to detect and/or quantitate the level of squamous cell carcinoma specific antigens expression in the biological sample. The antibody itself may be detectably labeled with a radioactive, flourescent, calorimetric or enzyme label. Such antibodies include the monoclonal antibodies AD6, 5C6, AD7, and AH1. Alternatively, the kit may contain a labeled secondary antibody.

5.4 Therapeutic Uses of Monoclonal Antibodies

The antibodies of the present invention may be used therapeutically in a variety of different ways. The monoclonal antibodies may be used in unmodified, i.e., non-conjugated form, to treat subjects having squamous cell carcinoma. For example, the antibodies may be used to direct complement (CDC) or effector cell (ADCC) mediated cytotoxicity. Alternatively, the antibodies may be conjugated to anti-tumor drugs, toxins or radionuclides. Conjugated antibodies can be administered to patients to achieve enhanced tumoricidal effects through the cytotoxic action of the chemotherapeutic agent delivered to the tumor based on the binding affinity of the antibody moiety.

Chimeric antibody molecules of the present invention may be prepared containing a mouse antigen-binding domain with human constant region domains (Morrison et al., 1984, *Proc. Natl Acad. Sci. U.S.A.* 81:6851; Takeda et al., 1985, *Nature*, 314:452) and this approach may be used to generate novel antibody molecules with desirable effector functions such as the ability to activate human complement and mediate ADCC.

The present invention relates to pharmaceutical compositions comprising the antibodies of the present invention. Amounts and regimens for the administration of antibodies, their fragments or derivatives can be determined readily by those with ordinary skill in the clinical art of treating cancer. For example, administration may be by parenteral, subcutaneous, intravenous, intramuscular, intraperitoneal, transdermal or buccal routes. Alternatively, or concurrently, administration may be by the oral route. The dosage administered will be dependent upon the age, health, and weight of the recipient, frequency of treatment and the nature of the effect desired.

Compositions within the scope of the invention include all compositions wherein the antibody, fragment or derivative is contained in an amount effective to achieve its intended purpose. While individual needs vary, determination of optimal ranges of effective amounts of each component is within the skill of the art. The effective dose is a function of the individual chimeric or monoclonal antibody, the presence and nature of a conjugated therapeutic agent, the patient and his clinical status and can vary from about 10 ng/kg body weight to about 100 mg/kg body weight. The preferred dosages comprise 0.1 to 10 mg/kg body weight. Preparations of the antibody, fragment or derivative of the present invention for parental administration, such as in detectably labeled form for imaging or in a free or conjugated form for therapy, include sterile lyophylized protein, aqueous or non-aqueous solutions, suspensions and emulsions. Examples of non-aqueous solvents are propyleneglygol, polyethyleneglycol, vegetable oil such as olive oil, and injectable organic esters such as ethyloleate. Aqueous carriers include water, alcoholic/aqueous solutions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, such as those based on Ringer's dextrose and the like. Preservatives and other additives may also be present, such as, for example, anti-microbials, antioxidants, chelating agents, and inert gases and the like. See, generally, *Remington's Pharmaceutical Science*, 16th ed., Mack Publishing Co., Easton, Pa., 1980.

In particular, the antibodies, fragments and derivatives thereof are useful for treating a subject having a squamous cell carcinoma. Such treatment comprises parenterally administering a single or multiple doses of the antibody, fragment or derivative, or conjugate thereof.

The novel antigens of the invention to which the antibodies AD6, 5C6, AD7 and AH1 bind may also be used for therapeutic applications. The antigens can be purified from tumors and administered, alone as an immunogen, or together with a proper immunological adjuvant. Alternatively, the antigens may be recombinantly produced for use as an immunogen.

6. EXAMPLE

Production of Squamous Cell Carcinomaspecific Monoclonal Antibodies

The subsection below describes the generation of monoclonal antibodies reactive against specific glycoproteins expressed on the surface of squamous cell carcinoma. Immunological assays indicate that the monoclonal antibodies react with carcinoma cells, while showing none or limited reactivity with normal tissue. In addition AH1 and AD7.

6.1 Preparation of Monoclonal Antibodies

Monoclonal antibodies (mAb) against human squamous cell lung carcinoma associated antigens (SLAA) were produced using a modified method described by Herzenberg et al. Four weeks old Balb/c mice were immunized by intra peritoneal (ip) injection with 100 µg of partially purified SLAA obtained from the membrane extracts from pooled human squamous cell lung carcinomas removed from patients at the time of surgery, emulsified with 200 µl of complete Freund's adjuvant. Two ip injections emulsified in 200 µl of incomplete Freund's adjuvant were given at 2 week intervals. Mice were then boosted intravenously with 20 µg of the immunogen and the splenocytes were removed 3 days later. Somatic hybrids were prepared using the mouse non-secreting myeloma cell line SP2/0-Ag14 following the procedue of Muraro et al. Hybridoma supernatents were assayed for specific antibody production in ELISA using several human squamous cell lung carcinoma cell lines (P3, P6 and H595) and partially purified immunogen. All hybridoma cell lines were cloned twice by limited dilution.

For ascities fluids production, four week old Balb/c mice were pristane-primed and then inoculated with approximately 5×106 hybridoma cells. mAb was purified from murine ascite fluids by protein G affinity chromatography. The protein content of purified antibody preparation was analyzed on a 12% SDS-polyacrylamide Tris-glycine gel.

6.2 Characterization of Monoclonal Antibodies 6.2.1. Western Blots

Western Blots were performed using the 5C6, AD6, AD7 and Ah1 antibodies. The protein samples were derived from lung lavage specimens. Samples (3 µg) were loaded onto 12% SDS PAGE. Proteins were transferred to nitrocellulose membranes and stained using antibodies labeled with horseradish peroxidase. As indicated in FIG. 1, the monoclonal antibodies of the invention each reacted against different antigens expressed within squamous cell carcinomas derived from lung lavage specimens.

6.2.2. ADCC with Squamous Cell Carcinoma Specific Antibodies

A four hour $^{51}$Cr release assay was used to measure ADCC activity. Target cells were the lung squamous CA cell line H596. Target cells were labeled with 200 μCi sodium [$^{51}$Cr] chromate (250-500 mCi/mg, Amersham, Arlington, Ill.) in 200 μl fetal calf serum for 1 hour. Target cells ($1 \times 10^4$) were incubated in 96 U-bottom wells of assay plates with effector cells in a ratio of effector to target cells of 80:1 in the presence of mAb (1.0 μg/well). The plates were incubated fro 4 hrs at 37° C. in a humidified atmosphere containing 5% CO2. Supernatant was harvested for gamma counting with the use of Skatron Harvester frames. Specific lysis was calculated with the use of the following formula:

Specific Lysis (%) =
$$\frac{Observed\ release\ (cpm) - spontaneous\ release\ (cpm)}{Total\ release\ (cpm) - spontaneous\ release\ (cpm)} \times 100$$

Spontaneous release was determined by measuring the radioactivity released from target cells incubated in medium alone. Total releasable radioactivity was obtained after treatment with 2.5% Triton X-100. Spontaneous release of radiolabeled chromium was measured after treatment with 2.5% Triton X-100.

As indicated in FIG. 2 and FIG. 3 the AH-1, D6 and 5C6 monoclonal antibodies demonstrated ADCC activity when tested against human squamous cell lung carcinoma cells. As presented in FIG. 3B, the ADCC activity was specific for human squamous cell lung carcinoma cells as indicated by the lack of activity against human colon carcinoma cells.

6.2.3. Immunohistochemistry Using Squamous Cell Carcinoma Specific Antibodies Staining protocols were as follows:

Mayo Frozen Tissue Protocol

Slides were fixed in 1% paraformaldehyde for 10 minutes followed by rinsing 3× in PBS. A blocking step was carried out with endogenous peroxidase (1% sodium azide +3% H$_2$O$_2$ and rinsed in water for 1 minute. 5% NGS was added for 10 minutes followed by a addition of primary antibody diluted in 1% NGS (2 μg/ml) and incubation for two hours at RT. Slides were rinsed 2-3× PBS and incubated for 15 minutes at RT with Biotin RAM (DAKO). The slides were rinsed 2-3× with PBS. Streptavidin(HRP) was added to the slides and incubated for 15 minutes at RT. The slides were rinsed twice with PBS and once with water. DAB or AEC.

Paraffin Section Protocol

Slides were placed at 60 degrees for 20 minutes. Deparaffinizing was done in the hood: (i) Xylene, 5 min; (ii) Xylene & 1% Iodine, 5 min: Xylene, 10 dips; (iii) 100% alcohol;(iv) 95% alcohol; and (v) 50% alcohol. Slides were placed in 50% methanol/50% 3% H$_2$O$_2$ for 10 min. and rinsed in water for 1 min. 5% NGS was added for 10 minutes followed by addition of primary antibody diluted in 1% NGS (1 μg/ml) and incubation overnight at RT. Samples were rinsed in water and incubated with Biotin GAM (DAKO) for 30 min at RT. Slides were rinsed in water and incubated with Streptavidin (HRP) for 30 minutes (DAKO). Samples were rinsed and water and DAB/AEC.

The four monoclonal antibodies of the invention were found to be reactive against antigens specifically expressed on the surface of squamous cell carcinomas of the lung (FIG. 4) but not on the surface of normal cells. In addition, the antibodies were found to be immunoreactive against antigens expressed on the surface of cervical carcinoma cells (FIGS. 7A-B).

In addition ELISA assays were performed using the following protocol. Lung lavage was coated with dilution neat, 1:2, 1:4, 1:8, 1:16, 1:32, 1:64, 1:128, 100 μl/well at 4° overnight. The wells were washed 3× with TBST. Blocking was carried out with TBST /2% gelatin (200 100 μl/well at 37° for one hour followed by washing 5× with TBST. 100 μl/well of ascites antibody was added and incubated for 1 hr at 37°. Anti-mouse IgG AP 1:1000 was added and incubated for 1 hr at 37°. The wells were washed 5× with TBST. Substrate P-NPP was added to each well and the endpoint was read at 405 nm. As indicated in FIGS. 5 and 6 the 5C6, and AD6 monoclonal antibodies reacted with lung lavage tissue samples.

In addition, cell flow cytometry was performed to test the specificity of the antibodies. Cells (LS174T, H596, H441 and CaLu3) grown to log phase in culture medium free of phenyl red and removed from flasks with 0.025% trypsin EDTA (BioWhittaker). The cells were then washed with PBS (pH7.4) and ssuspended in culture medium for 30 minutes and counted. All subsequent procedures were performed at 4° C.

The cells were washed three times with PBS. A sample containing $5 \times 10^5$ cells was suspended in 200 μl of PBS and delivered to each reaction tube. A solution of 200 μl of biotinylated antibody was added to the samples and the mixture was incubated at 4° C. for 30 min. The cells were washed three times with PBS and suspended in 500 μl of PBS. The cells are then analyzed by flow cytometry. As indicated in FIG. 8, lung carcinoma cells (H596, H441 and CaLu3) stained with the antibodies while little staining was observed for the control colon carcinoma cells (LS174T).

6.3 Vaccine Studies

Membrane preparations were obtained from pooled allogeneic lung cancer cells, i.e., squamous cell carcinomas. Membrane extracts were obtained from viable cells which were then subjected to low frequency sonication. The soluble material was separated on Sephadex G-200 and further subjected to discontinuous polyacrylamide gel electrophoresis. Individual bands isolated from the gels and tested for DHR (delayed cutaneous hypersensitivity) as described above were pooled and used as a vaccine. Skin testing for DHR employed 30 μg antigen (TAA). Sephadex fraction I was eliminated from the vaccine because this fraction contained inhibitory material which suppressed the immune response. The vaccine for therapy utilized 300 μg antigen in 0.2 ml complete Freund Adjuvant. In no instance was there evidence of an autoimmune pulmonary response. In each patient an enhancement of cell mediated and humoral immunity was observed. DHR continued to enhance over 5 years. 80% of the patients studied (237 in study) survived after surgery and vaccination versus 40% for surgery alone.

6.4 Cloning and Determination of the AD7 and 5C6 Heavy and Light Chains

The following primers are used for cloning and amplification of the AD7 and 5C6 heavy chain V-region:

(i) cDNA: MHCGSP1A:

5'-CAT GGA GTT AGT TTG GGC AGC AGA-3' (SEQ ID NO:1) Abridged Anchor Primer;

5'-GGC CAC GCG TCG ACT AGT ACG GGIIGG GII GGG IIG-3' (SEQ ID NO:2)

(ii) Amplification: MHCGSP2A:
    5'-CAG GGG CCA GTG GAT AGA CAG ATG-3' (SEQ ID NO:3)
    Abridged Anchor Primer;
    5'-GGC CAC GCG TCG ACT AGT ACG GGIIGG GII GGG IIG-3' (SEQ ID NO:2)

The following primers are used for cloning and amplification of the AD7 and 5C6 light chain V-region:

(i) cDNA: MLCGSP1:
    5'-CCT GTT GAA GCT CTT GAC AAT GGG-3' (SEQ ID NO:4)
    Abridged Anchor Primer;
    5'-GGC CAC GCG TCG ACT AGT ACG GGIIGG GII GGG IIG-3' (SEQ ID NO:2)

(ii) amplification: MOSKAPPA:
    5'-ACT GGA TGG TGG GAA GAT GGA T-3' (SEQ ID NO:5)
    Abridged Anchor Primer;
    5'-GGC CAC GCG TCG ACT AGT ACG GGIIGG GII GGG IIG-3' (SEQ ID NO:2)

6.5. Construction and Expression of Human-Mouse Chimeric Antibody Genes

Retroviral vectors pLHCXII and pLNCXII are used for the cDNA expression of the chimeric heavy chain and light chains respectively. pLNCXII is the vector LNCX except that an EcoRI site in the backbone of the vector is destroyed while another EcoRI site located 45 basepairs 5' to the neo gene is retained. LNCX was obtained from Dr. D. Miller (Fred Hutchinson Cancer Research Center, Seattle Wash.). The vector is derived from N2 vector by replacing the 5' long terminal repeats (LTR) of M-MuLV with M-MSV LTR and inserting a BalI/Xma III fragment containing the human cytomegalovirus (HCMV) immediate early promoter 3' to the neo gene. A polylinker containing HindIII, Hpa I and Cla I site is inserted 3' to the HCMV promotor for cloning of the target gene. The vector pLHCXII is made by replacing a −1.2 KbEcoR1/BarnH1 fragment carrying the neomycin resistant gene with a 1.4 kb BamH1/BamH1 fragment carrying a gene conferring hygromycin resistance. For generating the retroviral expression construct of pLNCXIIHuK, a DNA fragment carrying the cDNA encoding chimeric k chain (mAb) is obtained from its pBluescript construct by cleavage with Sma I/Cla I. The resulting fragment is cloned in Hpa I/Cla I linearized pLNCXII vector. Similarly, the DNA fragment sequences encoding the chimeric heavy chain is obtained from the pBluescript construct except that the plasmid is cleaved with Xba I, the sticky ends will be filled in by Klenow, and the fragment is excised by subsequent cleavage with HindIII. The fragment generated is cloned in HindIII/Hpa I linearized pLHCXII to generate pLHXII HuG1, the expression construct of chimeric mAb heavy chain.

For the development of chimeric mAb, the HC and LC expression constructs are sequentially introduced into SP2/O cells by electroporation, using the cell-porator system. Electroporation is carried out as follows. Briefly, SP2/O cells are washed in serum free DMEM with 4.5 g/L glucose (JRH Bioscience, Lenexa, Kans.) and suspended in the same medium at a concentration of $5 \times 10^6$ cells/ml. One hundred µg of the plasmid is added to 1 ml of the cell suspension in a electroporating chamber at 4° C. The cells and DNA mixture are pulsed at 650V/cm for 13 ms (capacitance setting at 1,600 µF). Cells are kept at 4° C. for 10 min and diluted in RPMI1640 medium containing 15% FCS. Cells are then distributed in 24 well plates at a concentration $5 \times 10^5$ cell per well. After incubation at 37° C. in 15% $CO^2$ incubator for 24 hour, selective medium containing hygromycin or active G418 at concentration of 500 µg/ml and 800 µg/ml respectively is added.

Human mouse chimeric mAb (Hu mAb) producing clones are grown in protein free hybridoma medium PFHM-II (G1BCO,BRL) and are purified by protein G affinity chromatography. Protein concentration are determined using Bio-Rad microassay procedure or by method of Lowry. The protein is analyzed on a pre-cast 4-20% SDS-polyacrylamide Tris-glycine gel (Novex System, San Diego, Calif.) with and without denaturation with 2-mercaptoethanol. The protein gel is visualized by staining with Coomassie Brilliant Blue R250 according to the method of Lamemmli.

The present invention is not to be limited in scope by the specific embodiments described herein which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the claims. Various publications are cited herein, the contents of which are hereby incorporated, by reference, in their entireties.

The invention claimed is:

1. A monoclonal antibody that binds to squamous cell carcinoma cells wherein the monoclonal antibody is mouse monoclonal antibody 5C6 as deposited with the American Type Culture Collection and assigned accession number PTA-2458.

2. The antibody according to claim 1 which is detectably labeled.

3. The antibody according to claim 2 wherein said detectable label is a radiolabel.

4. A fusion protein comprising the antigen binding region of monoclonal antibody 5C6, as deposited with the American Type Culture Collection and assigned accession number PTA-2458.

5. The fusion protein according to claim 4 which is detectably labeled.

6. The fusion protein according to claim 5 wherein said detectable label is a radiolabel.

7. The fusion protein according to claim 4 which is a human-mouse chimeric antibody.

* * * * *

SEQUENCE LISTING

```
<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1
catggagtta gtttgggcag caga                                          24

<210> SEQ ID NO 2
<211> LENGTH: 36
<212> TYPE: DNA
```

```
-continued

<213> ORGANISM: Artificial Sequence
<220> FEATURE:
<223> OTHER INFORMATION: Synthetic oligonucleotide
<221> NAME/KEY: misc_feature
<222> LOCATION: 24, 25, 29, 30, 34, 35
<223> OTHER INFORMATION: n = Inosine

<400> SEQUENCE: 2
ggccacgcgt cgactagtac gggnngggnn gggnng                              36

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
caggggccag tggatagaca gatg                                           24

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 4
cctgttgaag ctcttgacaa tggg                                           24

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 5
actggatggt gggaagatgg at                                             22
```